(12) United States Patent
Jordan et al.

(10) Patent No.: US 7,090,865 B2
(45) Date of Patent: Aug. 15, 2006

(54) COMPOSITION AND METHOD FOR TREATING AUTOIMMUNE HEMOLYTIC ANEMIA

(75) Inventors: Michael Jordan, Denver, CO (US); Philippa Marrack, Denver, CO (US); John Kappler, Denver, CO (US)

(73) Assignee: National Jewish Medical and Research Center, Denver, CO (US)

( * ) Notice: Subject to any disclaimer, the term of this patent is extended or adjusted under 35 U.S.C. 154(b) by 612 days.

(21) Appl. No.: 10/307,203

(22) Filed: Nov. 27, 2002

(65) Prior Publication Data

US 2003/0118637 A1  Jun. 26, 2003

Related U.S. Application Data

(60) Provisional application No. 60/334,326, filed on Nov. 29, 2001.

(51) Int. Cl.
*A61K 9/127* (2006.01)

(52) U.S. Cl. .................... 424/450; 514/102; 514/169
(58) Field of Classification Search ............... 424/450; 514/102, 169
See application file for complete search history.

(56) References Cited

U.S. PATENT DOCUMENTS 4,137,309 A  1/1979  Van Duzee ............... 424/204
6,689,747 B1 *  2/2004  Filvaroff et al. ............... 514/3

OTHER PUBLICATIONS

Akpek et al., *Amer. J. Hemtology*, 61:98-102 (1999).
Alves-Rosa et al., *Blood*, 96(8):2834-3840 (2000).
Fossati-Jimack et al., *J. Exp. Med.*, 190(11):1689-1696 (1999).
Huitinga et al., *J. Exp. Med.*, 172:1025-1033 (1990).
Naito et al., *J. Leukoc. Biol.*, 60:337-344 (1996).
Oldenborg et al., *Science*, 288:2051-2054 (2000).
Palermo et al., *Clin. Exp. Immunol.*, 116:462-467 (1999).
Pinto et al., *J. Leukoc. Biol.*, 49:579-586 (1991).
Pullon et al., *Bone*, 12:89-92 (1991).
Rodan, *Annu. Rev. Pharmacol. Toxicol.*, 38:375-88 (1998).
Sokol et al., *Acta haemat*, 72:245-257 (1984).
van Rooijen et al., *J. Leukoc. Biol.*, 45:97-104 (1989).

* cited by examiner

*Primary Examiner*—Gollamudi S. Kishore
(74) *Attorney, Agent, or Firm*—Sheridan Ross P.C.

(57) ABSTRACT

Disclosed are a composition and method to treat or prevent antibody-induced anemia and particularly, autoimmune hemolytic anemia. The composition comprises a bisphosphonate and a pharmaceutically acceptable carrier. In a preferred embodiment, the composition comprises clodronate and a liposome carrier.

21 Claims, 9 Drawing Sheets

COMPOSITION AND METHOD FOR TREATING AUTOIMMUNE HEMOLYTIC ANEMIA

CROSS-REFERENCE TO RELATED APPLICATIONS

This application claims the benefit of priority under 35 U.S.C. § 119(e) from U.S. Provisional Application Ser. No. 60/334,326, filed Nov. 29, 2001. The entire disclosure of U.S. Provisional Application Ser. No. 60/334,326 is incorporated herein by reference.

GOVERNMENT SUPPORT

This invention was supported in part with funding provided by Grant Nos. AI-17134, AI-18785 and AI-22295, each awarded by the United States Public Health Service (USPHS). The government may have certain rights to this invention.

FIELD OF THE INVENTION

This invention generally relates to a method of treating antibody-induced anemia, and particularly, autoimmune hemolytic anemia. The invention includes the administration of a bisphosphonate to a patient having such a disease, and particularly, liposomal clodronate. The invention also relates to compositions comprising a bisphosphonate and a second agent for the treatment of antibody-induced anemia.

BACKGROUND OF THE INVENTION

Autoimmune hemolytic anemia (AIHA) is an autoimmune disease in which antibodies against the patients own red blood cells (RBC's) lead to their premature destruction (Ware et al., Autoimmune Hemolytic Anemia. In: David G Nathan, Stuart H Orkin, ed. Hematology of Infancy and Childhood (5th ed). Philadelphia: W. B. Saunders; 1998: 499–522, incorporated by reference herein in its entirety). Anemia can be sudden and life threatening, or more gradual in onset. Though most cases are idiopathic, association with other forms of autoimmunity, malignancy, or infection is common (Ware et al., ibid.; Schreiber *J Rheumatol.* 7:395–397 (1980); Diehl et al., *Semin Oncol.* 25:80–97 (1998); Saif, *AIDS Patient Care STDS.* 15:217–224 (2001)). AIHA occurs in both children and adults, with a wide age distribution.

AIHA can be mediated by IgG, IgM, or, rarely, IgA antibodies (Ware et al., supra). Most clinically significant cases, however, are caused by IgG antibodies (Ware et al., supra; NIH conference. Pathophysiology of immune hemolytic anemia. *Ann Intern Med.* 87:210–222 (1977); Hashimoto, *Clin Rev Allergy Immunol.* 16:285–295 (1998)). In these patients, autoantibodies bind to RBC's and lead to their uptake by splenic and hepatic macrophages via Fc receptors (Izui et al., *J Exp Med.* 173:15–30 (1994)). Though IgG antibodies can fix complement, the principle means of destruction of RBC's in these cases is via phagocytosis (Ware et al., supra; Fossati-Jimack et al., *J Exp Med.* 191:1293–1302 (2000); Fossati-Jimack et al., *J Exp Med.* 190:1689–1696 (1999)). Therefore, even though B-cells (often with T-cell help) are producing the offending autoantibody, macrophages are essential effector cells for the development of anemia. This fact is reflected in therapy for AIHA. Splenectomy and corticosteroids, mainstays of treatment, both ultimately interfere with the phagocytosis of opsonized RBC's, among other effects (Ware et al., supra; Izui et al., supra). Experimental therapy in animal models has also utilized the specific blocking of Fc-mediated uptake of RBC's by either genetic means or the use of anti-Fc antibodies (Hazenbos et al., *Immunity* 5:181–188 (1996); Hazenbos et al., *J Immunol.* 161:3026–3032 (1998); Meyer et al., *Blood* 92:3997–4002 (1998); Schiller et al., *Eur. J Immunol.* 30:481–490 (2000); Clynes et al., *Immunity* 3:21–26 (1995)).

The current mainstays of standard therapy for AIHA (e.g., transfusion, corticosteroids, and, eventually, splenectomy) have many drawbacks. Transfusion have well described risks which accompany their use in AIHA patients. Corticosteroids have a multitude of well-known, undesirable acute and chronic effects. They also have another shortcoming. The onset of action of corticosteroids is variable, frequently taking many hours (or days) (Ware et al., supra). In patients who present with very severe anemia this shortcoming is a major source of concern and potential morbidity. In multiple case series, patients such as these, presenting with severe anemia (hemoglobin less than 6 g/dl), are quite common (Sokol et al., *Acta Haematol.* 72:245–257 (1984); Buchanan et al., *J Pediatr.* 88:780–783 (1976); Heisel et al., *Am. J Pediatr. Hematol. Oncol.* 5:147–152 (1983)).

Splenectomy, another mainstay of treatment, has many drawbacks as well. The most obvious one is routine surgical morbidity and mortality. This makes splenectomy unavailable as a therapy for certain unstable or frail patients. Another drawback of splenectomy is its association with a life-long risk of fatal sepsis from encapsulated microorganisms (Bell, *Semin Hematol.* 37:22–25 (2000); Hansen et al., *Pediatr Dev Pathol.* 4:105–121 (2001)). Finally, splenectomy does not always alleviate AIHA, because hepatic macrophages may be responsible for a significant proportion of RBC consumption (Katkhouda et al., *Ann Surg.* 228: 568–578 (1998); Akpek et al., *Am J Hematol.* 61:98–102 (1999)). In fact, the substantial role of hepatic Kupffer cells in the development of AIHA has been repeatedly shown in mice (Izui et al., *J Exp Med.* 173:15–30 (1994); Fossati-Jimack et al., *J Exp Med.* 191:1293–1302 (2000); Fossati-Jimack et al., *J Exp Med.* 190:1689–1696 (1999); Azeredo et all, *J. Exp. Med.* 195:665–672 (2002). The unpredictable efficacy of splenectomy is particularly concerning in light of the short term (surgical) and life-long (infectious) morbidity of this procedure.

Therefore, there is a need in the art for safer, more effective methods for treatment of autoimmune hemolytic anemia and related diseases.

SUMMARY OF THE INVENTION

One embodiment of the invention relates to a method to treat or prevent antibody-induced anemia. The method includes administering a composition comprising bisphosphonate and a pharmaceutically acceptable carrier to a patient that has, or is at risk of developing, antibody-induced anemia. In one aspect, the antibody-induced anemia is autoimmune hemolytic anemia (AIHA). In another aspect, the patient has or is at risk of developing acute autoimmune hemolytic anemia.

The bisphosphonate used in the present method can be selected from, but is not limited to, clodronate (dichloromethylene diphosphonate), alendronate, etidronate, tiludronate, pamidronate, ibandronate, zoledronic acid, and risedronate, and biologically active analogs (i.e., derivatives)

thereof. In one aspect, the bisphosphonate is clodronate (dichloromethylene diphosphonate) or a biologically active analog thereof.

In one aspect of the present method, the pharmaceutically acceptable carrier is a liposome. The liposome can include, but is not limited to, a lipid comprising cholesterol.

In one aspect, the composition is administered to the patient by a route of administration selected from, but not limited to, intraperitoneal, intravenous, subcutaneous or oral. In one aspect, the composition is administered at intervals of from about 1 to 2 weeks.

Preferably, the bisphosphonate is administered in an amount sufficient to reduce the numbers of splenic and hepatic phagocytic macrophages in the patient by at least about 10%. In one aspect, the composition is administered in an amount that reduces clearance of opsonized red blood cells in the patient within about 1 hour of administration of the composition, as compared to in the absence of the composition. In another aspect, the composition is administered in an amount that reduce red blood cell depletion in the patient by at least about 5%, as compared to in the absence of the composition. In another aspect, the bisphosphonate is administered in an amount of at least about 1 ml of the composition comprising about 0.7M bisphosphonate per kg body weight of the patient. In another aspect, the bisphosphonate is administered in an amount of from about 1 ml to about 10 ml of the composition comprising about 0.7M bisphosphonate per kg body weight of the patient. In yet another aspect, the bisphosphonate is administered in an amount of at least about 1 mg per kg body weight of the patient.

The method can additionally include administration of a corticosteroid. In one aspect, the patient has had or will have a splenectomy.

Another embodiment of the invention relates to a composition for the treatment of antibody-induced anemia, comprising a bisphosphonate and a corticosteroid. In one aspect, the bisphosphonate is complexed with a liposome. The bisphosphonate can be selected from, but is not limited to, clodronate (dichloromethylene diphosphonate), alendronate, etidronate, tiludronate, pamidronate, ibandronate, zoledronic acid, and risedronate, and biologically active analogs thereof.

BRIEF DESCRIPTION OF THE DRAWINGS OF THE INVENTION

DETAILED DESCRIPTION OF THE INVENTION

Figure 1A:
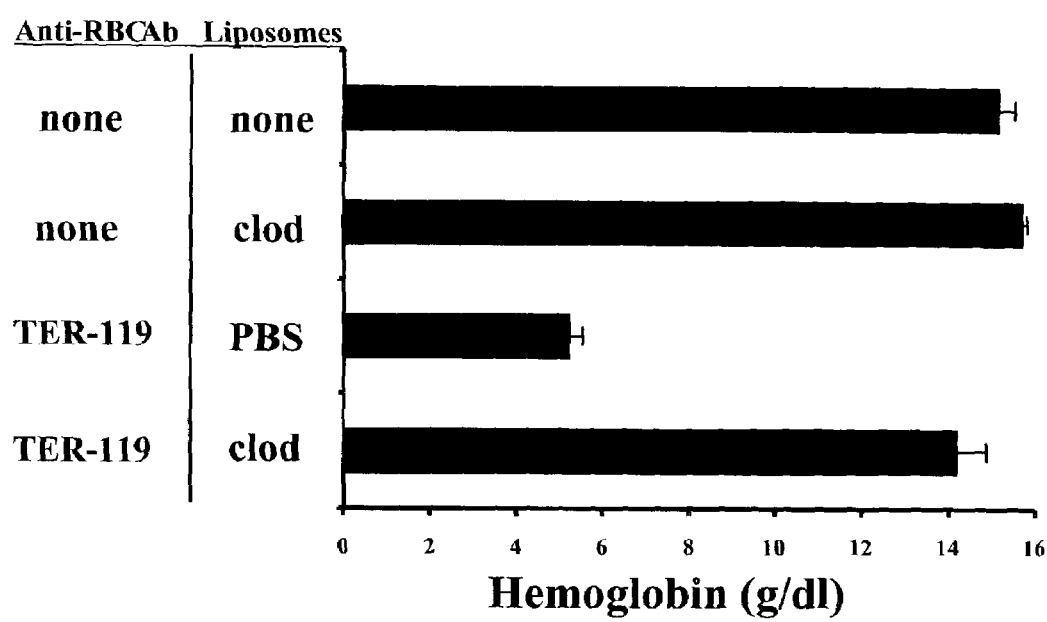
FIG. 1A is a bar graph showing that liposomal clodronate prevents the development of anemia induced by TER-119.

The present invention generally relates to a method to treat or prevent antibody-induced anemia and particularly, autoimmune hemolytic anemia (AIHA). The method includes the step of administering to a patient that has or is at risk of developing antibody-induced anemia a composition comprising a bisphosphonate and a pharmaceutically acceptable carrier. In a preferred embodiment, the pharmaceutically acceptable carrier is a liposome.

Bisphosphonates operate by inhibiting the function of osteoclasts. There is evidence for both a direct blocking effect on these cells and an apoptosis-inducing effect (Rodan, *Annu Rev Pharmacol Toxicol.* 38:375–388 (1998); Rogers et al., *Bone,* 24:73S–79S (1999); Russell et al., *Osteoporos Int.* 9:S66–80 (1999)). One bisphosphonate is clodronate (also referred to herein as dichloromethylene diphosphonate). Clodronate has been used for treating osteolytic bone diseases and osteoporosis. Over a decade ago it was found that incorporation of this drug into liposomes allowed it to become a potent anti-macrophage agent both in vivo and in vitro (van Rooijen et al., *Cell Tissue Res.* 238:355–358 (1984); Claassen et al., *J Immunol Methods,* 134:153–161 (1990)). The liposomal drug is taken up by macrophages and rapidly causes apoptosis (van Rooijen et al., *J Immunol Methods,* 193:93–99 (1996); Schmidt-Weberet al., *J Leukoc Biol.,* 60:230–244(1996); Naito et al., *J Leukoc Biol.* 60:337–344 (1996)). Its effects in vivo are principally influenced by its route of administration. Injection into tissues leads to the depletion of macrophages from the tissue itself and from draining lymph nodes. Intravenous injection of liposomally encapsulated clodronate leads to near complete depletion of splenic (and hepatic) macrophages and marginal zone dendritic cells within 24 hours (van Rooijen et al., *J Immunol Methods,* 174:83–93 (1994)). Unlike other methods of macrophage depletion, however, this treatment does not lead to the secretion of proinflammatory cytokines by the dying macrophages (van Rooijen et al., *J Leukoc Biol.,* 62:702–709 (1997)). Moreover, liposomal clodronate appears to have a very selective effect on macrophages and phagocytic dendritic cells. Neutrophils and lymphocytes have not been found to be directly affected by the drug (van Rooijen et al., 1994, supra; van Rooijen et al., *J Leukoc Biol.* 45:97–104 (1989); Alves-Rosa et al., *Blood.* 96:2834–2840 (2000)).

The present inventors investigated whether the potent and specific anti-macrophage effects of liposomal clodronate could be harnessed to treat autoimmune hemolytic anemia. To study this question, the inventors generated a model of AIHA in mice. The results of the inventors'experiments demonstrated that liposomal clodronate was a very effective therapy for AIHA in this model.

As discussed above, liposomal clodronate has been described as a potent antimacrophage agent (van Rooijen et al., 1984, supra). It has, therefore, been investigated as a potentially useful drug for treating autoimmune disorders in animal models such as adjuvant arthritis, uveitis, and experimental autoimmune encephalitis (Huitinga et al., *J Exp Med.* 172:1025–1033 (1990); Tran etal., *J Immunol.* 161:3767–3775(1998); Broekhuyse et al., *Exp Eye Res.*

65:841–848 (1997); Oelzner et al., *Inflamm Res.* 49:424–433 (2000); Richards et al., *Rheumatology* 40:978–987 (2001)). More recently, it was found to be useful in a mouse model of immune thrombocytopenic purpura (Alves-Rosa et al., 2000, supra). These autoimmune diseases have different etiologies and different conventional therapeutic treatments. However, prior to the present invention, to the present inventors' knowledge, liposomal clodronate had not been taught or suggested for use in treating antibody-induced anemia, and particularly, for treating spontaneous autoimmune hemolytic anemia (AIHA).

The experiments detailed herein show that liposomal clodronate consistently halts red blood cell destruction in an animal model of AIHA. It is effective when given prior to antibody challenge, as well as when given concurrently, in a more chronic fashion. It protects against the development of anemia, despite the fact that virtually all circulating RBC's are antibody-coated. Liposomal clodronate failed to protect against IgM-mediated, macrophage-independent, anemia. In addition to its striking potency, it has an extremely rapid onset of action. Furthermore, a single depleting dose is sufficient to protect mice from antibody-induced RBC destruction for 1–2 weeks. These characteristics are all very desirable for new agent to treat AIHA.

Autoimmune hemolytic anemia is a highly variable disease. It can be caused by a wide variety of IgG and/or IgM antibodies. Numerous underlying conditions have been associated with it. Furthermore, its natural history is also quite variable. While many patients present with a slowly developing anemia, others, including the majority of patients in pediatric case series, present with sudden, severe anemia (Sokol et al., *Acta Haematol.* 72:245–257 (1984); Carapella et al., *Vox Sang.* 36:13–20 (1979); Buchanan et al., *J. Pediatr.* 88:780–783 (1976)). The present inventors have attempted to model this disorder by administering a variety of anti-RBC antibodies in both a chronic and acute fashion. The inventors utilized a xenogeneic rat-derived antibody and a mouse-derived IgG monoclonal antibody and obtained similar results. This model mimics several aspects of the disease and is believed to be an appropriate one for studying anti-macrophage agents in this disease.

The conventional approaches to treatment of autoimmune hemolytic anemia (see Background) have many drawbacks, discussed in detail above. Liposomal clodronate offers many potential advantages over current therapy. With its swift and potent ability to shut-off RBC consumption, liposomal clodronate may reasonably be thought of as a temporary medical splenectomy, but without surgical considerations and surgical morbidity or mortality. In the experiments described in the Examples section, it completely halted the uptake of opsonized RBC's by the spleen, as a splenectomy would be expected to do. However, because the spleen is not removed in the method of the present invention, its function is eventually restored by the natural replenishment of macrophages. In addition, the speed of onset of liposomal clodronate appears to be superior to that of corticosteroids. This may prove to be particularly useful in cases of severe, life-threatening anemia, where cardiovascular compromise is evident. While liposomal clodronate is unlikely to replace corticosteroids, it is believed to be useful as an adjunctive therapy, allowing more rapid, reliable relief of RBC destruction. Another potential advantage of clodronate is its ability to block or deplete phagocytic macrophages outside of the spleen. Macrophages in the liver and bone marrow, which are not accessible by surgical means, are affected as well. Liposomal clodronate may ultimately be useful as an intermittent therapy for patients who continue to experience significant anemia after splenectomy.

Another important aspect of liposomal clodronate is its temporary (1–2 weeks for a single dose) duration of action. While cases of AIHA in adult patients are typically chronic, most pediatric case series report that approximately half of all warm autoantibody (IgG-mediated) AIHA cases are "acute", lasting less than 6 months. Accordingly, there may be situations in both adult and pediatric patients where temporary ablation of splenic function is desirable, but where life-threatening loss of splenic function is not necessary. The use of liposomal clodronate is expected to improve the medical management of AIHA, and some patients may thereby avoid splenectomy and its life-long consequences.

The present inventors have shown that liposomal clodronate is effective when given repeatedly and concurrently with anti-RBC antibody challenge. This "chronic" administration raises the possibility that liposomal clodronate could be administered repeatedly over a long period of time, and thus supplant other medical and surgical therapies. Indeed, liposomal clodronate could conceivably be used intermittently as a steroid-sparing agent in chronic cases of AIHA. If administered only once every 1–2 weeks, it would be a very practical intravenous therapy to administer.

Moreover, liposomal clodronate has been found to have no apparent direct effects on cells other than mononuclear phagocytes (van Rooijen et al., 1997, supra). No alterations in circulating lymphocytes or neutrophils have been reported. Furthermore, in the present inventors' experiments (see Examples) using dye-labeled liposomal clodronate, nearly all dye-containing cells within the spleen or liver were $CD68^+$. This result indicates that no cells other than mononuclear phagocytes received a significant dose of the drug. Finally, in short-term experimental models of infection, liposomal clodronate actually protects animals from mortality (Kooguchi et al., *Infect. Immun.* 66:3164–3169 (1998); Leemans et al., *J. Immunol.* 166:4604–4611 (2001); Nieuwenhuijzen et al., *Ann. Surg.* 218:791–799 (1993); Savoy et al., *Infect. Immun.* 65:1800–1807 (1997); Wijburg et al., *Eur. J Immunol.* 30:944–953 (2000)), indicating that liposomal clodronate will be safer than other conventional therapies for AIHA at least in the short term.

Accordingly, one component of a composition useful in the method of the present invention is a bisphosphonate. Although the present inventors have performed experiments using clodronate encapsulated in liposomes, it is believed that other bisphosphonates will also be effective, combined with a pharmaceutically acceptable carrier that facilitates the delivery of the bisphosphonate to a macrophage and entry into the macrophage. According to the present invention, a bisphosphonate is a pyrophosphate analog in which a carbon atom replaces the central atom of oxygen (i.e., having a P—C—P backbone). This carbon substitution makes these compounds resistant to hydrolysis, and allows two additional chains of variable structure. One of these side chains usually contains a hydroxyl moiety, which allows high affinity for calcium crystals and bone mineral (noting the prevalent use to treat bone disease). The differences at the other side chain produce marked differences in the antiresorptive potency of different bisphosphonates. Newer bisphosphonates, such as ibandronate and zoledronic acid, show 10,000–100,000-fold greater potency than do the older agents such as etidronate (Berenson et al., "The Role Of Bisphosphonates In Multiple Myeloma", for the American Society of Clinical Oncology Bisphosphonates Expert Panel (2002)). Bisphosphonates are well-known in the art, and are reviewed or described, for example, in: Body, *Eur. J. Cancer* 34:263–9 (1998); Fleisch, *Endocr. Rev.* 19:80–100 (1998); Vasikaran, *Ann Clin Biochem* 38(Pt 6):608–623 (2001); Niemi et al., *Int. J. Pharmaceutics* 174:111–115 (1998); Niemi et al., *Eur. J. Phamaceut. Sci.* 11:173–180 (2000); van Gelder et al., *Bone* 16:511–520 (1995); Diez-Perez, *Maturitas* 43:19–26 (2002); each of which is incorporated by reference in its entirety.

Worldwide, seven bisphosphonates (clodronate (dichloromethylene diphosphonate), alendronate, etidronate, tiludronate, pamidronate, ibandronate, zoledronic acid) are available for various conditions. Prior to 2001, pamidronate intravenous (IV) was approved in the United States for treatment of metastatic bone disease. In February 2002, the U.S. Food and Drug Administration (FDA) approved the use of zoledronic acid for the treatment of patients with multiple myeloma and other metastatic bone disease. Roche Pharmaceuticals, the makers of clodronate, which is available in both IV and oral forms, will soon be seeking FDA approval. In Canada, both pamidronate and clodronate are approved for use in patients with metastatic bone disease. See Berenson et al., 2002, ibid.

Therefore, the bisphosphonate for use in the present invention can be any bisphosphonate. Preferably, the bisphosphonate, when delivered into a macrophage, prevents clearance of opsonized red blood cells by the macrophage and, even more preferably, causes apoptosis of the macrophage. In a preferred embodiment, the bisphosphonate does not lead to the secretion of proinflammatory cytokines by the dying macrophages. In another embodiment, the bisphosphonate preferably acts on macrophages and phagocytic dendritic cells, and not on neutrophils and lymphocytes. Particularly preferred bisphosphonates for use in the present invention include, but are not limited to, clodronate (dichloromethylene diphosphonate), alendronate, etidronate, tiludronate, pamidronate, ibandronate, zoledronic acid, and risedronate, as well as any biologically active derivatives (analogs) of such bisphosphonates. In one embodiment, the bisphosphonate used in the present invention is clodronate or a biologically active derivative thereof.

According to the present invention, a biologically active derivative or analog of a bisphosphonate is any compound that is able to mimic the biological activity of a given bisphosphonate, often because the derivative has a basic structure that mimics the basic structure of the given bisphosphonate and/or has the salient biological properties of the given bisphosphonate compound. Biological activity can be measured using any suitable assay known in the art, including by evaluating any chemical or biological activity of the compound, such as those described in Body, 1998, supra; Fleisch, 1998, supra; Vasikaran, 2001, supra; Niemi et al., 1998, supra; Niemi et al., 2000, supra; van Gelder et al., 1995, supra; Diez-Perez, 2002, supra.

Such derivatives can be designed, selected and/or otherwise identified using a variety of methods known in the art. Various methods of drug design, useful to design therapeutic compounds are disclosed in Maulik et al., 1997, *Molecular Biotechnology: Therapeutic Applications and Strategies*, Wiley-Liss, Inc., which is incorporated herein by reference in its entirety. A bisphosphonate derivative can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In general, the biological activity or biological action of a compound refers to any function(s) exhibited or performed by the compound as measured or observed in vivo (i.e., in the natural physiological environment in which the compound acts) or in vitro (i.e., under laboratory conditions). Modifications of a compound, such as by creation of a derivative of such a compound, may result in compounds having the same biological activity as the lead compound, or in compounds having decreased or increased biological activity as compared to the lead compound. As discussed above, bisphosphonate is a pyrophosphate analog in which a carbon atom replaces the central atom of oxygen (i.e., having a P—C—P backbone), and the various compounds within the type (which can include derivatives) are typically distinguished by two additional chains of variable structure. Indeed, bisphosphonates are considered to be derivatives of pyrophosphate and therefore, a derivative of a given pyrophosphate is also considered to be derivatives of pyrophosphate. As such, derivatives of bisphosphonates can meet the minimum definition of a bisphosphonate above (a pyrophosphate analog in which a carbon atom replaces the central atom of oxygen (i.e., having a P—C—P backbone)).

According to the present invention, a composition of the present invention also includes a pharmaceutically acceptable carrier. As used herein, a pharmaceutically acceptable carrier refers to any substance or vehicle suitable for delivering a bisphosphonate useful in a method of the present invention to a suitable in vivo or ex vivo site. Such a carrier is preferably capable of allowing the bisphosphonate component of the composition to come into contact with phagocytic cells (preferably splenic or hepatic macrophages) in the patient and even more preferably, to be introduced into the phagocytic cells. Preferred pharmaceutically acceptable carriers are capable of maintaining a bisphosphonate in a form that, upon arrival of the bisphosphonate to a cell or tissue, the bisphosphonate is capable of contacting a cell of interest (i.e., a phagocytic cell, such as a macrophage) and preferably, of entering the cell, whereby the bisphosphonate can inhibit the ability of the phagocytic cell to clear opsonized red blood cells, or more preferably, whereby the bisphosphonate can induce the phagocytic cell to undergo apoptosis.

A pharmaceutically acceptable carrier can include a pharmaceutically acceptable excipient. Suitable excipients of the present invention include any excipients or formularies useful for in vivo delivery. Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable pharmaceutically acceptable carriers for bisphosphonate compounds of the invention include, but are not limited to, liposomes or other lipid-containing vehicles, antibodies (e.g., the bisphosphonate compound is linked to the antibody), liquid injectables or solids which can be taken up in a suitable liquid as a suspension or solution for injection, liquids that can be aerosolized, capsules, or tablets. In a non-liquid formulation, the excipient can comprise, for example, dextrose, human serum albumin, and/or preservatives to which sterile water or saline can be added prior to administration. Natural lipid-containing delivery vehicles include cells and cellular membranes. Artificial lipid-containing delivery vehicles include liposomes and micelles. A delivery vehicle can be modified to target to a particular site in a patient, thereby targeting and making use of the bisphosphonate at that specific site. Suitable modifications include manipulating the chemical formula of the lipid portion of the delivery vehicle and/or introducing into the vehicle a targeting agent (e.g., an antibody or peptide) capable of specifically targeting a delivery vehicle to a preferred site, for example, a preferred cell type (e.g., a macrophage).

A liposome delivery vehicle comprises a lipid composition that is capable of delivering a bisphosphonate or derivative thereof to a suitable cell and/or tissue in a patient. A liposome delivery vehicle comprises a lipid composition that is capable of fusing with the plasma membrane of the target cell (e.g., a phagocytic cell) to deliver the bisphosphonate or derivative thereof into a cell. As discussed above, liposome delivery vehicles can be modified to target a particular site in a mammal (i.e., a targeting liposome), thereby targeting and making use of a bisphosphonate or derivative thereof at that site. Suitable modifications include manipulating the chemical formula of the lipid portion of the delivery vehicle. Manipulating the chemical formula of the lipid portion of the delivery vehicle can elicit the extracellular or intracellular targeting of the delivery vehicle. For example, a chemical can be added to the lipid formula of a liposome that alters the charge of the lipid bilayer of the liposome so that the liposome fuses with particular cells having particular charge characteristics. In one embodiment, other targeting mechanisms, such as targeting by addition of exogenous targeting molecules to a liposome (i.e., antibodies) may not be a necessary component of the liposome of the present invention, since effective delivery of the bisphosphonate can already be provided by the composition (e.g., if the bisphosphonate selectively acts on phagocytic cells, but not neutrophils or lymphocytes) without the aid of additional targeting mechanisms. However, in some embodiments, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., 1986, *Biochemistry* 25: 5500–6; Ho et al., 1987a, *J Biol Chem* 262: 13979–84; Ho et al., 1987b, *J Biol Chem* 262: 13973–8; and U.S. Pat. No. 4,957,735 to Huang et al., each of which is incorporated herein by reference in its entirety). In one embodiment, if avoidance of the efficient uptake of injected liposomes by reticuloendothelial system cells due to opsonization of liposomes by plasma proteins or other factors is desired, hydrophilic lipids, such as gangliosides (Allen et al., 1987, *FEBS Lett* 223: 42–6) or polyethylene glycol (PEG)-derived lipids (Klibanov et al., 1990, *FEBS Lett* 268: 235–7), can be incorporated into the bilayer of a conventional liposome to form the so-called sterically-stabilized or "stealth" liposomes (Woodle et al., 1992, *Biochim Biophys Acta* 1113: 171–99). Variations of such liposomes are described, for example, in U.S. Pat. No. 5,705,187 to Unger et al., U.S. Pat. No. 5,820,873 to Choi et al., U.S. Pat. No. 5,817,856 to Tirosh et al.; U.S. Pat. No. 5,686,101 to Tagawa et al.; U.S. Pat. No. 5,043,164 to Huang et al., and U.S. Pat. No. 5,013,556 to Woodle et al., all of which are incorporated herein by reference in their entireties).

Suitable liposomes for use with the present invention include any liposome. Some preferred liposomes of the present invention include those liposomes commonly used in, for example, drug methods known to those of skill in the art. Liposomes can include, but are not limited to, lipids comprising cholesterol and cationic liposomes, and can be provided in any form, including, but not limited to, multilamellar vesicles (MLVs), small unilamellar vesicles (SUVs) or extruded lipids (Templeton et al., 1997, *Nature Biotech.*, 15:647–652).

Complexing a compound, such as a bisphosphonate, with a liposome is accomplished in a straightforward manner using techniques known in the art and described in the Examples, for example. The compound can be effectively complexed with the liposome simply by gently mixing the compound and the liposome together, preferably in a suitable excipient. The compound can also be incorporated into the liposome as the liposome is formulated (e.g., rehydrated). For example, lipids can be dissolved in a solvent and lyophilized, followed by rehydration in a liquid solution of bisphosphonate. An example of preparation of lipids and bisphosphonate is described in the Examples section. A complex of liposome and a bisphosphonate can be referred to herein as liposomal bisphosphonate, for example. A suitable amount of liposome to use in the present composition is from about 0.1 nmol liposomes to about 100 nmol liposomes (or any other suitable amount of liposomes, which can be determined by the skilled artisan) per amount of bisphosphonate to be added to a composition.

A liposome delivery vehicle is preferably capable of remaining stable in a mammal for a sufficient amount of time to deliver a bisphosphonate and other compounds, if included, to a preferred site in the patient. A liposome carrier is preferably stable in the patient into which it has been administered for at least about 30 minutes, more preferably for at least about 1 hour and even more preferably for at least about 24–72 hours.

One type of pharmaceutically acceptable carrier includes a controlled release formulation that is capable of slowly releasing a composition of the present invention into an patient. As used herein, a controlled release formulation comprises a bisphosphonate or derivative thereof in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems.

In one aspect of the invention, the composition to be administered to the patient can include additional components that assist in the delivery of the bisphosphonate to the patient, that stabilize the bisphosphonate, or that provide an additional benefit to the patient that has, or is at risk of developing, antibody-induced anemia. For example, the composition can include a corticosteroid (oral, inhaled or injected), which is a compound that is conventionally used to treat autoimmune hemolytic anemia. Corticosteroids are well-known in the art and suitable corticosteroids for treatment of patients with antibody-induced anemia are all encompassed by the present invention. The corticosteroid or other agent need not necessarily be administered as a part of the same composition containing the bisphosphonate, but can be administered in a separate composition at an appropriate time relative to the administration of the bisphosphonate-containing composition.

Accordingly, the method of the present invention preferably prevents or treats antibody-induced anemia in a patient such that the patient is protected from the antibody-induced anemia. As used herein, the phrase "protected from a disease" refers to reducing the symptoms of the disease, reducing the occurrence of the disease, and/or reducing the severity of the disease. Protecting a patient can refer to the ability of a therapeutic composition of the present invention, when administered to a patient, to prevent a disease from occurring and/or to cure or to alleviate disease symptoms, signs or causes. As such, to protect a patient from a disease includes both preventing disease occurrence or recurrence (prophylactic treatment) and treating a patient that has a disease or that is experiencing initial symptoms or later stage symptoms of a disease (therapeutic treatment). In particular, protecting a patient from a disease is accomplished by reducing the ability of phagocytic cells in the patient, and particularly macrophages (preferably splenic and hepatic macrophages), to clear opsonized red blood cells, and/or increasing the apoptosis of such cells in the patient. The term, "disease" refers to any deviation from the normal health of a patient and includes a state when disease symptoms are present, as well as conditions in which a deviation has occurred, but symptoms are not yet manifested.

More specifically, a composition as described herein, when administered to a patient by the method of the present invention, preferably produces a result which can include alleviation of the disease (e.g., reduction of at least one symptom or clinical manifestation of the disease), elimination of the disease, prevention of the disease, or alleviation of a secondary disease resulting from the occurrence of a primary disease.

According to the present invention, an effective administration protocol (i.e., administering a composition of the invention in an effective manner) comprises suitable dose parameters and modes of administration that result in a reduction in the clearance of red blood cells (i.e., opsonized red blood cells) from the patient by phagocytic cells, or an increase in the apoptosis of such phagocytic cells in the patient that has or that may develop antibody-induced anemia, preferably so that the patient is protected from the disease (e.g., by disease prevention or prevention of disease recurrence, or by alleviating one or more symptoms of ongoing disease). Effective dose parameters can be determined using methods standard in the art for the disease. Such methods include, for example, determination of survival rates, side effects (i.e., toxicity) and progression or regression of disease.

In accordance with the present invention, a suitable single dose size is a dose that results in the above-identified responses in a patient when administered one or more times over a suitable time period. Doses can vary depending upon the patient (age, health, other symptoms), the form of the disease being treated (e.g., acute or chronic), the carrier used, and/or the route of administration. For example, in the treatment of acute disease, a suitable dose regimen can be a single dose, whereas in chronic patients, a suitable dose regimen can be multiple doses of smaller amount, at intervals of days or weeks. One of skill in the art can readily determine appropriate single dose sizes for a given patient based on the size of a patient and the route of administration. One of skill in the art can monitor the effectiveness of the treatment by measuring, for example, hemoglobin and red blood cell counts.

A suitable single dose of a composition of the present invention is an amount that is sufficient to reduce, eliminate, or prevent at least one symptom of antibody-induced anemia, or to reduce, eliminate or prevent a biological activity that contributes to the disease.

In one aspect of the invention, a suitable single dose of a composition of the present invention is an amount that, when administered by any route of administration, reduces phagocytic cells (and preferably splenic and/or hepatic phagocytic macrophages) in a patient, as compared to a patient which has not been administered with the composition of the present invention (i.e., a control patient), as compared to the patient prior to administration of the composition (also a control), or as compared to a standard established for the particular disease, patient type and composition (another type of control). In one embodiment, a suitable dose is an amount that reduces the number of phagocytic cells in the patient, as compared to the control, by at least about 10%, and more preferably at least about 15%, and more preferably at least about 20%, and more preferably at least about 25%, and more preferably at least about 30%, and more preferably at least about 35%, and more preferably at least about 40%, and more preferably at least about 45%, and more preferably at least about 50%, and more preferably at least about 55%, and more preferably at least about 60%, and more preferably at least about 65%, and more preferably at least about 70%, and more preferably at least about 75%, and more preferably at least about 80%, and more preferably at least about 85%, and more preferably at least about 90%, and more preferably at least about 95%. Measurement of phagocytic cells in a patient can be performed using techniques standard in the art.

In another embodiment, the composition of the present invention is administered in a dose that is effective to reduce clearance of opsonized red blood cells (RBC's) in the patient within about 1, 2, 3, 4, 5, 6, 7, 8, 9, 10, 11, 12, 13, 14, 15, 16, 17, 18, 19, 20, 21, 22, 23 or 24 hours of administration of the composition, as compared to the control as set forth above. Preferably, the composition is administered in a dose that is effective to reduce clearance of opsonized RBC's in the patient within the given time period by at least about 10%, and more preferably at least about 15%, and more preferably at least about 20%, and more preferably at least about 25%, and more preferably at least about 30%, and more preferably at least about 35%, and more preferably at least about 40%, and more preferably at least about 45%, and more preferably at least about 50%, and more preferably at least about 55%, and more preferably at least about 60%, and more preferably at least about 65%, and more preferably at least about 70%, and more preferably at least about 75%, and more preferably at least about 80%, and more preferably at least about 85%, and more preferably at least about 90%, and more preferably at least about 95%, and even more preferably about 100%. This measurement can be made as a measurement of overall numbers or as a rate of clearance, using techniques standard in the art.

In yet another embodiment, the composition of the present invention is administered in a dose that is effective to reduce the depletion of the number of red blood cells in the patient by at least about 5%, as compared to a control as discussed above. More preferably, the composition of the present invention is administered in a dose that is effective to reduce the depletion of the number of red blood cells in the patient by at least about 10%, and more preferably at least about 15%, and more preferably at least about 20%, and more preferably at least about 25%, and more preferably at least about 30%, and more preferably at least about 35%, and more preferably at least about 40%, and more preferably at least about 45%, and more preferably at least about 50%, and more preferably at least about 55%, and more preferably at least about 60%, and more preferably at least about 65%, and more preferably at least about 70%, and more preferably at least about 75%, and more preferably at least about 80%, and more preferably at least about 85%, and more preferably at least about 90%, and more preferably at least about 95%, and even more preferably about 100%. Measurement of red blood cell depletion in a patient can be performed using techniques standard in the art.

In one embodiment, a suitable dose of bisphosphonate to include in the composition is an amount that results in administration of at least about 0.1 ml of a composition per kg body weight of the patient, wherein the composition is between about 0.1M and 1M bisphosphonate. In another embodiment, the composition is at least about 0.1M bisphosphonate, and in another embodiment, the composition is at least about 0.2M bisphosphonate, and in another embodiment, the composition is at least about 0.3M bisphosphonate, and in another embodiment, the composition is at least about 0.4M bisphosphonate, and in another embodiment, the composition is at least about 0.5M bisphosphonate, and in another embodiment, the composition is at least about 0.6M bisphosphonate, and in another embodiment, the composition is at least about 0.7M bisphosphonate, and in another embodiment, the composition is at least about 0.8M bisphosphonate, and in another embodiment, the composition is at least about 0.9M bisphosphonate, and in another embodiment, the composition is at least about 1M bisphosphonate.

In another embodiment, a suitable dose of bisphosphonate to include in the composition is an amount comprising any of the above concentrations of bisphosphonate that results in administration of at least about 0.5 ml of a composition per kg body weight of the patient, and in another embodiment, at least about 1 ml of a composition per kg body weight of the patient, and in another embodiment, at least about 1.5 ml of a composition per kg body weight of the patient, and in another embodiment, at least about 2 ml of a composition per kg body weight of the patient, and in another embodiment, at least about 2.5 ml of a composition per kg body weight of the patient, and in another embodiment, at least about 3 ml of a composition per kg body weight of the patient, and in another embodiment, at least about 3.5 ml of a composition per kg body weight of the patient, and in another embodiment, at least about 4 ml of a composition per kg body weight of the patient, and in another embodiment, at least about 4.5 ml of a composition per kg body weight of the patient, and in another embodiment, at least about 5 ml of a composition per kg body weight of the patient, and in another embodiment, at least about 5.5 ml of a composition per kg body weight of the patient, and in another embodiment, at least about 6 ml of a composition per kg body weight of the patient, and in another embodiment, at least about 6.5 ml of a composition per kg body weight of the patient, and in another embodiment, at least about 7 ml of a composition per kg body weight of the patient, and in another embodiment, at least about 7.5 ml of a composition per kg body weight of the patient, and in another embodiment, at least about 8 ml of a composition per kg body weight of the patient, and in another embodiment, at least about 8.5 ml of a composition per kg body weight of the patient, and in another embodiment, at least about 9 ml of a composition per kg body weight of the patient, and in another embodiment, at least about 9.5 ml of a composition per kg body weight of the patient, and in another embodiment, at least about 10 ml of a composition per kg body weight of the patient.

In yet another embodiment, a suitable dose of bisphosphonate to include in the composition is an amount that results in administration of at least about 0.1 mg of a bisphosphonate per kg body weight of the patient, and in another embodiment, at least about 0.2 mg of bisphosphonate per kg body weight of the patient, and in another embodiment, at least about 0.3 mg of bisphosphonate per kg body weight of the patient, and in another embodiment, at least about 0.4 mg of bisphosphonate per kg body weight of the patient, and in another embodiment, at least about 0.5 mg of bisphosphonate per kg body weight of the patient, and in another embodiment, at least about 0.6 mg of bisphosphonate per kg body weight of the patient, and in another embodiment, at least about 0.7 mg of bisphosphonate per kg body weight of the patient, and in another embodiment, at least about 0.8 mg of bisphosphonate per kg body weight of the patient, and in another embodiment, at least about 0.9 mg of bisphosphonate per kg body weight of the patient, and in another embodiment, at least about 1 mg of bisphosphonate per kg body weight of the patient, and in another embodiment, at least about 1.1 mg of bisphosphonate per kg body weight of the patient, and in another embodiment, at least about 1.2 mg of bisphosphonate per kg body weight of the patient, and in another embodiment, at least about 1.3 mg of bisphosphonate per kg body weight of the patient, and in another embodiment, at least about 1.4 mg of bisphosphonate per kg body weight of the patient, and in another embodiment, at least about 1.5 mg of bisphosphonate per kg body weight of the patient, and so on, in increments of 0.1 mg, up to at least about 10 mg per kg body weight of the patient.

It will be obvious to one of skill in the art that the number of doses administered to a patient is dependent upon the extent of the disease and the response of an individual patient to the treatment. For example, an adult or a patient with chronic disease may require more doses or smaller or larger doses than a pediatric patient or a patient with chronic disease. Thus, it is within the scope of the present invention that a suitable number of doses includes any number required to treat a given disease and patient.

A preferred number of doses of a composition of the present invention in order to achieve the desired effect is at least one dose (e.g., in acute disease, a single dose can be sufficient), and in some patients, is at least about 2 or more doses (e.g., in chronic disease, multiple or continuous dosing may be necessary to control the disease). The typical interval between doses when more than one dose is required is at least about 3 days, and more preferably at least about 4 days, and more preferably at least about 5 days, and more preferably at least about 6 days, and more preferably at least about 7 days, and more preferably at least about 8 days, and more preferably at least about 9 days, and more preferably at least about 10 days, and more preferably at least about 11 days, and more preferably at least about 12 days, and more preferably at least about 13 days, and more preferably at least about 14 days. In one embodiment, the interval between doses is at least about 1 week. In another embodiment, the interval between doses is between about 1–2 weeks. In another embodiment, the interval between doses is at least about 2 weeks.

As discussed above, a composition of the present invention is administered to a patient in a manner effective to deliver the composition to a cell, a tissue, and/or systemically to the patient, whereby a reduction in clearance of opsonized red blood cells and/or an increase in the number of phagocytic cells responsible for such clearance that are undergoing apoptosis is achieved as a result of the administration of the composition. Suitable administration protocols include any in vivo or ex vivo administration protocol. The preferred routes of administration will be apparent to those of skill in the art, depending on the patient, the bisphosphonate, the pharmaceutically acceptable carrier, and the specific type of antibody-induced anemia to be prevented or treated. Preferred methods of in vivo administration include, but are not limited to, intravenous administration istration, intrasplenic administration, intraperitoneal administration, intramuscular administration, intradermal administration, intranodal administration, subcutaneous administration, intraarticular administration, intraventricular administration, oral, impregnation of a catheter, and direct injection into a tissue. Some particularly preferred routes of administration include, intravenous, intrasplenic, intraperitoneal, and subcutaneous. Combinations of routes of delivery can be used and in some instances, may enhance the therapeutic effects of the composition.

Ex vivo administration refers to performing part of the regulatory step outside of the patient, such as administering a composition (nucleic acid orprotein) ofthe present invention to a population of cells removed from a patient under conditions such that the composition contacts and/or enters the cell, and returning the cells to the patient. Ex vivo methods are particularly suitable when the target cell can easily be removed from and returned to the patient.

Many of the above-described routes of administration, including intravenous, intraperitoneal, intrasplenic, intradermal, and intramuscular administrations can be performed using methods standard in the art. Oral delivery can be performed by complexing a composition of the present invention to a carrier capable of withstanding degradation by digestive enzymes in the gut of an animal. Examples of such carriers, include plastic capsules or tablets, such as those known in the art.

One method of local administration is by direct injection. Direct injection techniques are particularly useful for administering a composition to a cell or tissue (e.g., spleen) that is accessible by surgery, and particularly, on or near the surface of the body. Administration of a composition locally within the area of a target cell refers to injecting the composition centimeters and preferably, millimeters from the target cell or tissue.

The composition and method of the present invention can be used to prevent and/or treat any patient that has, or is at risk of developing, any antibody-induced anemia, and particularly, any antibody-induced anemia in which phagocytic cells (e.g., macrophages and dendritic cells) phagocytose red blood cells. In particular, the method and composition of the present invention is useful for treating and/or preventing autoimmune hemolytic anemia (AIHA). Compositions of the invention can be administered to any member of the Vertebrate class, Mammalia, including, without limitation, primates, rodents, livestock and domestic pets. Preferred mammals to protect are humans.

In one embodiment, the patient to be treated has undergone, is undergoing, or will undergo any of the conventional therapeutic treatments for antibody-induced anemia known in the art. For example, the patient can undergo corticosteroid treatment, either simultaneously or alternating with the bisphosphonate treatment of the invention. A patient could receive corticosteroid treatment, and then a bisphosphonate treatment, and then, 1–2 weeks after the bisphosphonate treatment, additional corticosteroid treatment. Protocols for such combination treatment can be determined based on the steroid sensitivity to the patient, the responsiveness of the patient to one or the other treatment, and the overall improvement of the patient, for example.

In another embodiment, the patient can have a splenectomy, or be proceeding toward a splenectomy. As discussed above, the composition and method of the present invention can be very useful for patients that still suffer from anemia (e.g., as a result of the action of hepatic phagocytic cells) despite having had a splenectomy.

The following examples are provided for the purpose of illustration and are not intended to limit the scope of the present invention.

EXAMPLES

Materials and Methods

The following Materials and Methods were used in Examples 1–7 below. Flow cytometry/microscopy Mice. In all of the examples, female C57BL/6 mice and male A/J mice were obtained from The Jackson Laboratory (Bar Harbor, Me.). All mice used were 6–12 weeks of age. Intravenous injections were performed via the retroorbital plexus in mice anesthetized with tribromoethanol. If mice received two different injections sequentially, they were performed on opposite sides. All bleeding of mice was via the tail veins into EDTA/saline. A minimum of 3 mice were used per experimental group in all experiments. In time course experiments, no mouse was bled more than once, so that each time point represents at least 3 unique mice.

Antibodies. The anti-red blood cell antibodies used throughout these examples were Ter-119 (a generous gift of Dr I. Weissman), a rat IgG2b monoclonal antibody (Kina et al., *Br J Haematol.* 109:280–287 (2000)); 34-3C, a mouse IgG2a monoclonal antibody (Fossati-Jimack et al., 1999, supra), and 4C8, a monoclonal mouse IgM (Fossati-Jimack, 2000, supra). Ter-119 and 34-3C were affinity purified via protein G and protein A chromatography, respectively. 4C8 was purified using a HiTrap IgM purification column (Amersham Pharmacia, Uppsala, Sweden) per the manufacturer's protocol. Unless otherwise specified, the following doses ofthese antibodies were administered to experimental animals: TER-119: 50 µg i.p.; 34-3C: 150 µg i.p.; 4C8: 150 µg i.v. These doses were determined empirically to be non-lethal, yet produce significant anemia in healthy C57B1/6 mice after a single injection. For flow cytometry and microscopy, anti-CD68 (FA-11) and F4/80 were obtained from Serotec (Oxford, UK). FA-11 was either biotinylated or coupled to Oregon green using a commercial dye-coupling kit (Molecular Probes, Eugene, Oreg.).

Clodronate and Liposomes. Clodronate (dichloromethylene diphosphonate) was provided by Roche Diagnostics, Mannheim, Germany. Clodronate liposomes were prepared as previously described (Van Rooijen et al., 1994, supra). Briefly, 86 mg of phosphatidylcholine (Lipoid EPC; LIPOID, Ludwigshafen, Germany) and 8 mg of cholesterol (Sigma Chemical Co., St Louis, Mo.) were combined with 10 ml of a clodronate (0.7 molar) solution and sonicated gently. The resulting liposomes were then washed to eliminate free drug. Empty liposomes were prepared under the same conditions using phosphate buffered saline (PBS) instead of the clodronate solution. All liposomes were passed through a 12 micron filter immediately prior to use in order to eliminate large lipid aggregates. Unless otherwise specified, 10 ml of liposomes/kilogram of body weight (or 0.1 ml/10 grams) were administered intravenously in all experiments. This dose has been previously shown to eliminate splenic and hepatic macrophages in 24 hours (van Rooijen et al., 1984, supra). PKH labeling of liposomes was performed by incubating the liposomal solution with an equal volume of diluent C (Sigma Chemical Co, St Louis, Mo.) containing 16 micromolar PKH26 (Sigma) for 5 minutes. Liposomes were then washed by centrifugation prior to injection.

Flow Cytometry. For flow cytometry of whole blood, animals were bled via a tail vein into saline containing EDTA. Circulating CFSE+RBC numbers were determined via flow cytometry of whole blood. RBC's were defined by forward versus side scatter gating. Labeled cells were easily distinguished from unlabeled RBC's by CFSE fluorescence. Reticulocyte counts were determined by flow cytometry after staining with Auramine-O (Sigma Chemical Co). An absolute reticulocyte number was obtained by multiplying this percent value by the total RBC number. Quantification of RBC-bound antibody was determined by a flow cytometry-based method. RBC's were washed repeatedly in EDTA saline and then incubated with a Cy5 conjugated F(ab')2 goat anti-mouse/rat IgG reagent (Jackson Immunoresearch, West Grove, Pa.) and analyzed on a Facscaliber (Becton-Dickinson, San Jose, Calif.).

For examination of spleen or liver cells, tissues were dissected and treated with collagenase as follows. Organs were minced with sharp scissors and placed a solution (2 ml) of collagenase D (100 U/ml)(Boehringer Mannheim) and DNAse (0.1 mg/ml) (Sigma) for 30 minutes at 37° C. One ml of 0.1 m EDTA in PBS was then added and cells were incubated for another 5 minutes. The resulting cells and fragments were then passed through a 100 micron strainer. RBC's were subsequently lysed with buffered ammonium chloride. After immunostaining, cells were either analyzed via flow cytometry or cytospun onto slides for microscopy. For flow cytometry, Oregon green-coupled anti-CD68 was used after permeabilizing cells with saponin. For microscopy, biotinylated primary antibodies against CD68 or F4/80 were used, followed by a streptavidin Cy-5 secondary reagent. Intracellular staining for RBC's was achieved in permeabilized cells by staining with TNP-coupled Ter-119, followed by a (hamster) anti-TNP antibody (BD Pharmingen, San Diego, Calif.), and then a Cy-3 coupled rabbit anti-hamster polyclonal antibody (Jackson Immunoresearch, West Grove, Pa.). Nuclei were counterstained with Hoechst 33342 (Molecular Probes).

Preparation of RBC's. RBC's were opsonized in vitro with Ter-119 by incubating $10^9$ cells/ml with 2 µg/ml of antibody for 30 minutes. This dose was determined empirically as a non-agglutinating dose which labeled all cells (data not shown). Cells were then washed to remove any unbound antibody. Dye labeling with carboxyfluorescein succimidyl ester (CFSE)(Molecular Probes, Eugene, Oreg.) was performed as follows: $10^9$ washed cells /ml were incubated with 50 micromolar CFSE in saline for 15 minutes at 37° C. They were then washed again prior to reinjection. For labeling of RBC's with 1,1'-dioctadecyl-3,3,3',3'-tetramethylindodicarbocyanine, 4-chlorobenzenesulfonate (DiD) (Molecular Probes), cells were incubated at $10^9$/ml in diluent C (Sigma) with 2 micromolar DiD for 5 minutes at room temperature. They were then reinjected into donor mice 2–3 times until approximately 60% of the donor mouse's RBC's were labeled with dye. This mouse was then bled to provide a source of labeled RBC's. This passage through a second donor mouse was performed because it led to a significant decrease in spontaneous dye uptake by splenocytes of mice injected with non-opsonized RBC's.

Determination of hemoglobin and RBC counts. Blood hemoglobin concentrations were determined by a spectrophotometric method on a Sysmex NE1500. These values were correlated with RBC counts obtained on the same machine and on a Coulter Z1.

Example 1

The following example demonstrates that liposomal clodronate alleviates antibody-induced anemia.

To induce anemia, mice were injected with either Ter-119, an IgG2b monoclonal rat anti-mouse red blood cell antibody, or two different monoclonal autoantibodies derived from autoimmune NZB mice: 34-3C (IgG2a) or 4C8 (IgM). Doses and routes of administration for each antibody are described in the Materials and Methods above. Ter-119 recognizes a ubiquitous erythrocyte antigen expressed at highest levels with terminal differentiation (Kina et al., 2000, supra). After a single injection of any of these antibodies, anemia progressed for approximately 48–72 hours in otherwise untreated mice (data not shown).

Mice pretreated with PBS-containing liposomes develop severe anemia, as documented by a marked decrease in blood hemoglobin values, 36 hours after injection with Ter-119 (FIG. 1). This anemia was identical to antibody-challenged animals which received no pretreatment (data not shown). In contrast, pretreatment with liposomal clodronate largely prevented the development of this anemia. Injection of liposomal clodronate into otherwise unperturbed mice had no significant effect on the blood hemoglobin concentration, or the lymphocyte, neutrophil or platelet counts (FIG. 1A and data not shown).

Figure 1B:
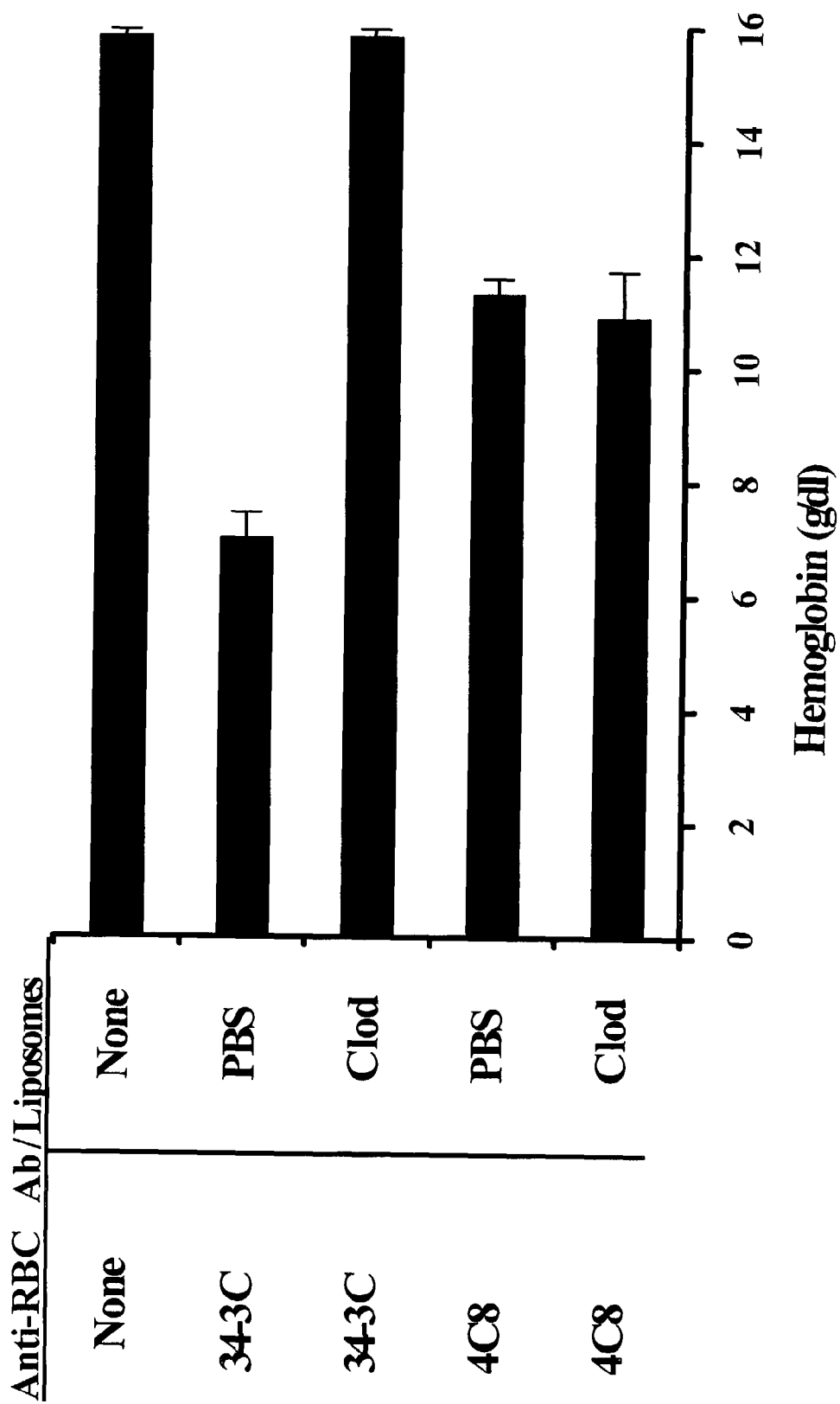
FIG. 1B is a bar graph showing that liposomal clodronate prevents the development of anemia induced by 34-3C.

Liposomal clodronate also efficiently prevented the development of anemia after injection of a true autoantibody, 34-3C (FIG. 1B). In contrast, the injection of a monoclonal IgM, 4C8, produced an anemia which was not affected by liposomal clodronate. This finding is consistent with the fact that the 4C8 IgM anti-RBC autoantibody causes anemia in a "macrophage-independent" way, as a result of a massive agglutination of RBC's in liver and spleen (Saif AIDS Patient Care STDS 15:217–224 (2001)).

Liposomal clodronate was effective at preventing the development of anemia, despite high levels of RBC-bound IgG (data not shown). At the same time animals were bled to assess anemia, an aliquot of blood was obtained to perform a flow cytometry-based Coombs assay. Representative assays from clodronate treated mice, challenged with either TER-119 or 34-3C were evaluated (data not shown). The amount of TBC-bound antibody on circulating RBC's correlated with the dose of antibody administered and with the degree of anemia in animals not treated with clodronate. Coombs assays performed on TER-119 treated animals were consistently higher than 34-3C treated animals, despite a higher administered dose of 34-3C. This fact is consistent with the higher affinity of TER-119. Coombs assays performed on mice in the PBS-liposome group revealed similar results (data not shown). Interestingly, however, the amount of RBC-bound antibody was moderately lower, consistent with the ongoing clearance of opsonized RBC's in these animals.

Example 2

The following example demonstrates that liposomal clodronate alleviates antibody-induced anemia when administered chronically.

Figure 2A:
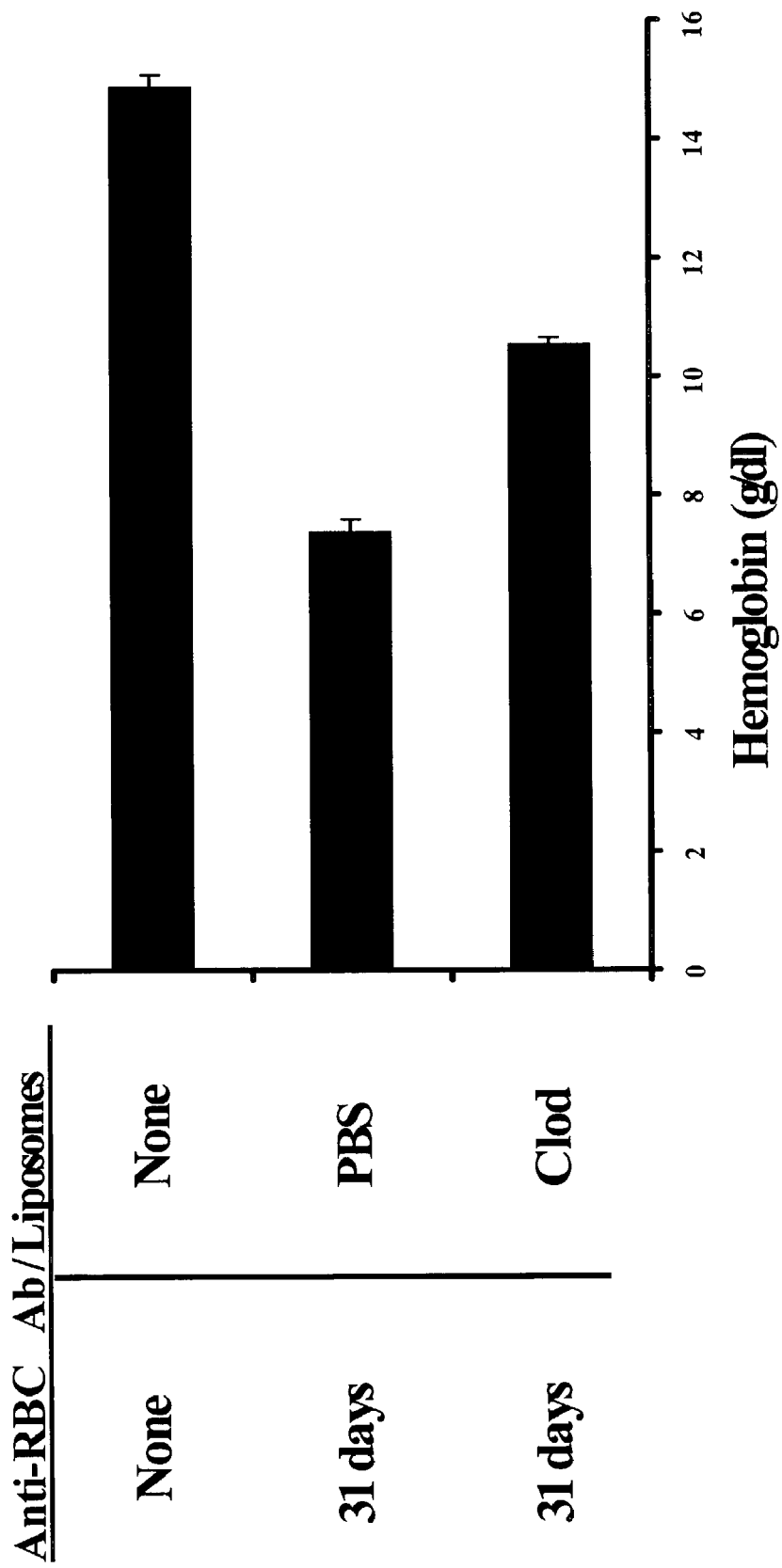
FIG. 2A is a bar graph showing that liposomal clodronate alleviates antibody-induced anemia (hemoglobin count shown) when administered chronically.
Figure 2B:
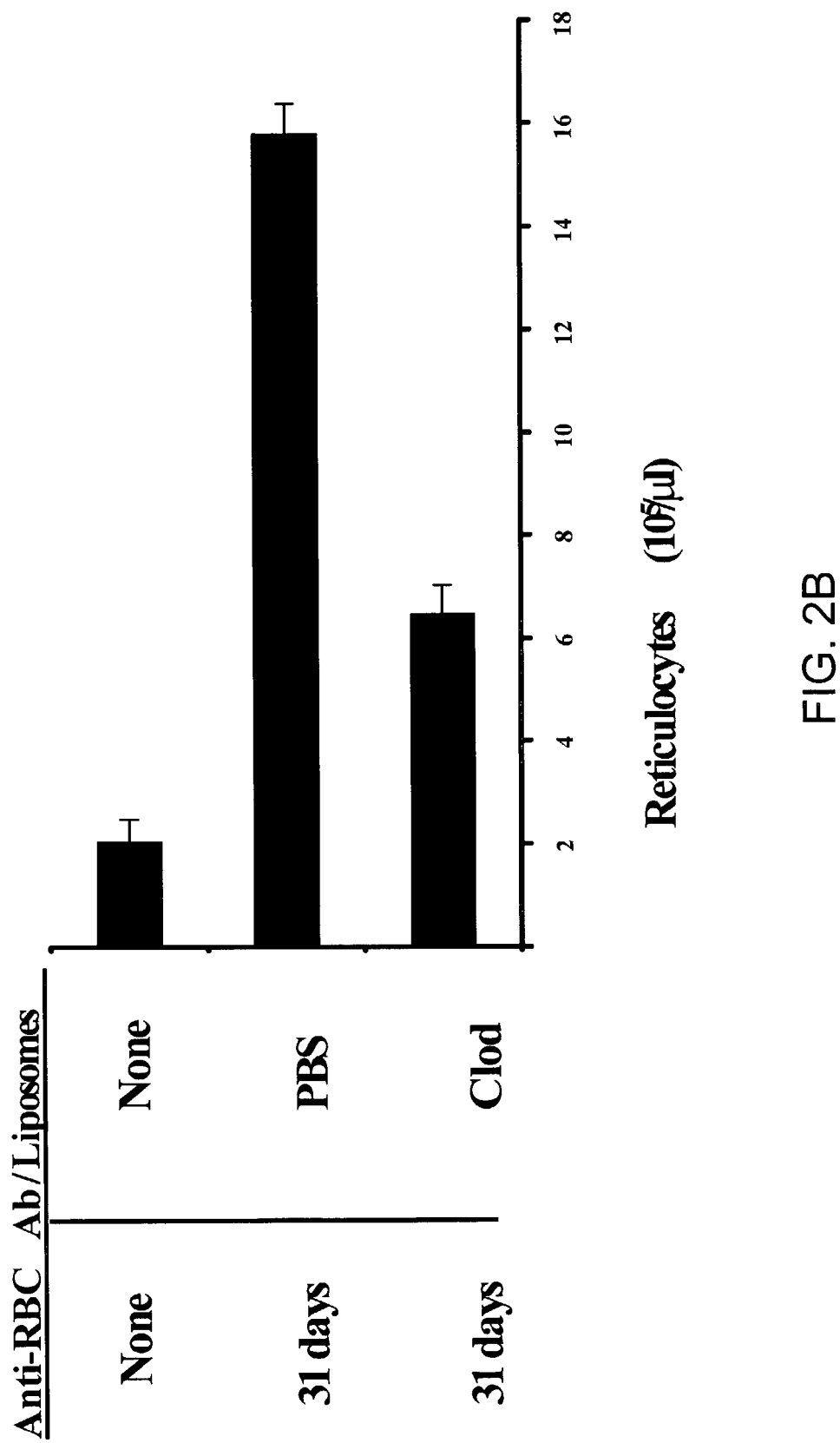
FIG. 2B is a bar graph showing that animals treated with PBS-liposomes have 2–3 fold higher reticulocytosis than animals treated with liposomal clodronate.

In order to assess whether liposomal clodronate could be a useful reagent in a more chronic setting, the following experiment was performed. Increasing doses of 34-3C were administered to A/J mice over a 31 day period. The weekly antibody doses were as follows: week one=70 µg; week two=105 µg; week three=14 µg; week four=175 µg; week five 105 µg (half week only). The weekly dose was split into two i.p. injections administered every three of four days. At the same time that the antibody injections were started, weekly liposome treatments were begun. Mice were given injections of either PBS or clodronate liposomes, once per week, for a total of 5 injections. At the end of a month, animals were bled to assess hemoglobin (FIG. 2A) and reticulocyte counts (FIG. 2B). Because their IgG allotype matches that of 34-3C, A/J mice were chosen for this experiment in order to avoid the development of neutralizing anti-allotypic antibody response.

All animals developed anemia in this experiment, but liposomal clodronate treated animals developed substantially less anemia. Furthermore, the difference in hemoglobin values between the two treatment groups could underestimate the difference in RBC consumption between them, because there was a significant compensatory reticulocytosis. Animals in the PBS treated group had 2–3 fold higher absolute reticulocyte counts (FIG. 2B). Similar to the experiments described in FIG. 1, all circulating RBC's in mice from either treatment group were positive for surface bound antibody (data not shown).

Example 3

The following example demonstrates that liposomal clodronate rapidly prevents the clearance of opsonized RBC's.

Figure 3A:
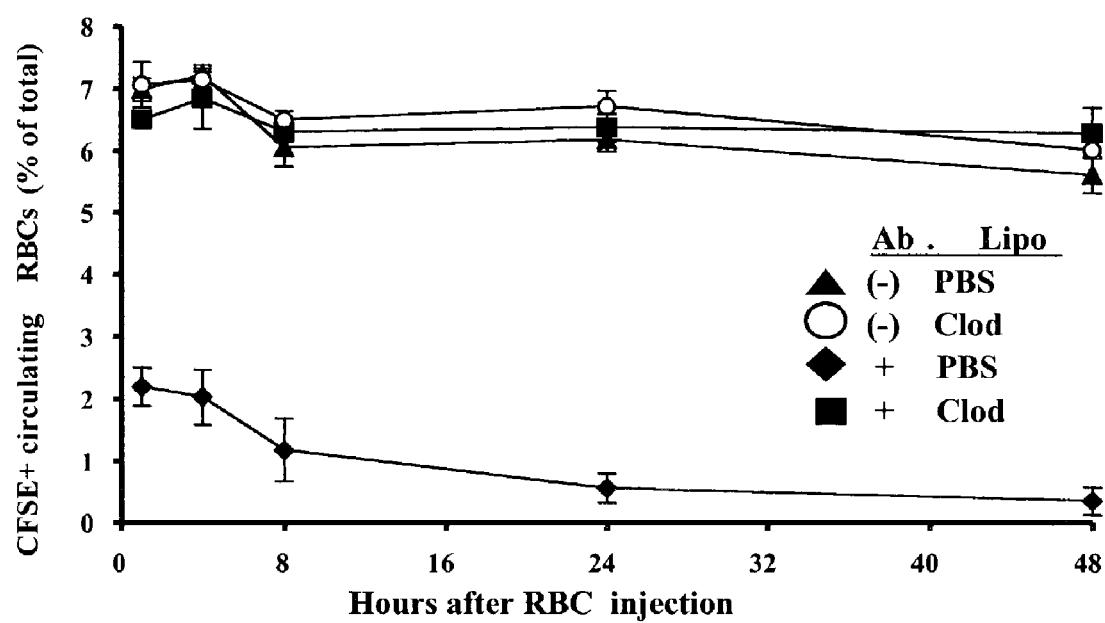
FIG. 3A is a line graph showing that pretreatment with liposomal clodronate prevents the clearance of opsonized, circulating red blood cells (RBC's).

To investigate further how liposomal clodronate inhibited the development of anemia, RBC's were labeled with the fluorescent dye, CFSE, and opsonized in vitro with anti-RBC antibody (Ter-119). These RBC's ($10^9$) were then injected into mice which had been treated with either PBS or clodronate-containing liposomes 36 hours previously. Control mice received an identical number of dye-labeled, but not opsonized RBC's. After allowing 1 hour for the RBC's to equilibrate in the peripheral circulation, mice were bled at various time points. Clearance of labeled RBC's from peripheral circulation was assessed by flow cytometry of blood specimens obtained at the indicated times (FIG. 3A). Data are expressed as a percent of circulating RBC's which are CFSE+(+/−standard error). The RBC's which were opsonized in vitro with antibody were found to be rapidly cleared from the circulating pool (FIG. 3A). Within one hour, >70% of these cells were removed from circulation. In contrast, mice pretreated with clodronate failed to clear any measurable number of antibody-coated RBC's from circulation for the length of the experiment (48 hours).

Figure 3B:
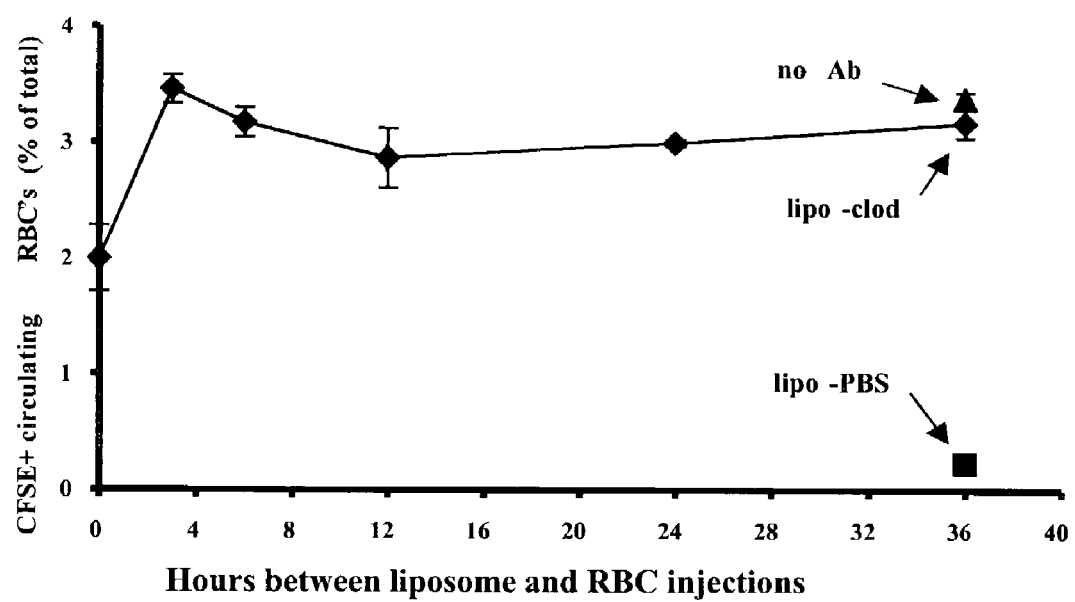
FIG. 3B is a line graph showing that liposomal clodronate acts rapidly to halt clearance of opsonized RBC's.

In order to determine how rapidly liposomal clodronate exerts its effects, the following experiment was performed. Mice were injected with identical numbers of dye-labeled, antibody-opsonized RBC's after receiving liposomal clodronate at various time points. They were bled 4 hours after the RBC injection. Clearance of labeled RBC's from peripheral circulation was assessed by flow cytometry of whole blood, obtained four hours after RBC injection. In the experiment above, pretreatment with clodronate 36 hours prior to injecting opsonized RBC's had been chosen because this interval allowed for efficient depletion of splenic and hepatic macrophages before challenge. As is apparent from FIG. 3B, liposomal clodronate very rapidly prevented clearance of opsonized RBC's. It completely prevented clearance when given only 3 hours before the RBC's. Furthermore, even if given at the same time as opsonized RBC's (sequentially, in opposite retroorbital injection sites) it was still able to prevent clearance of >60% of these cells. Together, the data in FIGS. 3A and 3B indicate that liposomal clodronate causes a significant decrease in opsonized RBC clearance in less than 1 hour after administration.

Example 4

The following example demonstrates that liposomal clodronate blocks phagocytosis by macrophages.

The inventors concluded that the clodronate was able to prevent the clearance of opsonized RBC's in these experiments because it destroyed the macrophages which would normally take up antibody-coated RBCs. However, in the studies described above, the clodronate surprisingly acted very quickly, within 1 hour, even though clodronate has not been reported to deplete macrophages from the spleen and liver of treated animals within this time frame (van Rooijen et al., 1984, supra; Claassen et al., 1990, supra; van Rooijen et al., 1996, supra; Naito et al., 1996, supra; van Rooijen et al., 1997, supra; van Rooijen et al., 1994, supra; van Rooijen et al., 1989, supra). To investigate this issue further, the following experiment was performed.

Mice were injected with either PBS or clodronate liposomes which had been labeled with the lipophilic dye, PKH26. Two hours later, they were injected with RBC's which had been labeled with another dye, DiD. Three hours after the RBC injection, the animals were sacrificed, and their liver and spleen cells were stained for CD68, a marker specific for mononuclear phagocytes (macrophages, dendritic cells, and monocytes). Most CD68+spleen or liver cells are macrophages, however, because they are more abundant than either dendritic cells or monocytes in these tissues (Steinman et al., *J Exp Med.* 141:804–820 (1975); Steinman et al., *J Exp Med.* 149:1–16 (1979)).

Figure 4:
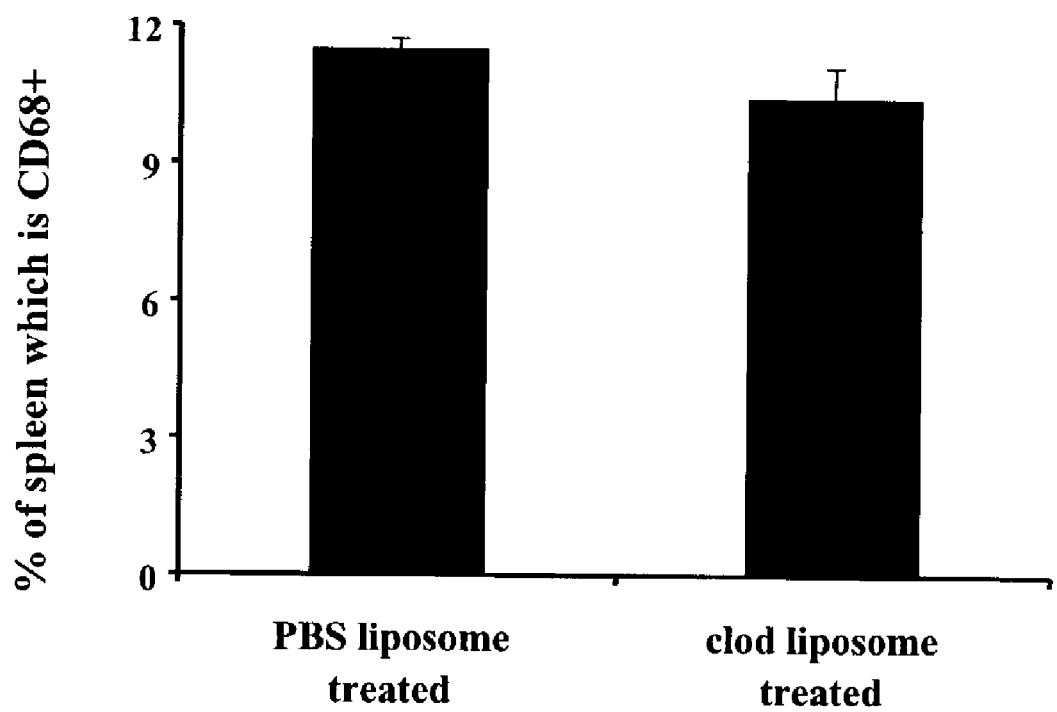
FIG. 4 is a bar graph showing that CD68+ spleen cells (macrophages, dendritic cells and monocytes) are not significantly depleted by liposomal clodronate at the 5 hour time point after administration.

As shown in FIG. 4, liposomal clodronate does not significantly deplete macrophages (CD68+ cells) from the spleen within 5 hours. Similar results were seen in the liver (data not shown). This is in contrast to later time points (24 hours), where liposomal clodronate very thoroughly depletes spleen and liver macrophages (data not shown and van Rooijen et al., 1984, supra; Claassen et al., 1990, supra; van Rooijen et al., 1996, supra; Naito et al., 1996, supra; van Rooijen et al., 1997, supra; van Rooijen et al., 1994, supra; van Rooijen et al., 1989, supra)). Therefore, even though liposomal clodronate does not deplete macrophages within the first few hours, it has a potent ability to prevent the clearance of opsonized RBC's within this same time frame (FIG. 3). This apparent contradiction is explained by a subsequent analysis.

The inventors examined CD68+ spleen or liver cells for uptake of PKH-labeled liposomes and uptake of DiD-labeled RBC's. Both PBS and clodronate liposomes are taken up efficiently by macrophages within 5 hours, as indicated by PKH fluorescence (data not shown). Some macrophages have also taken up opsonized RBC's as indicated by DiD fluorescence (data not shown). These double positive cells are particularly evident in the mice which were treated with PBS liposomes (data not shown). In contrast, the results showed that far fewer macrophages from clodronate treated mice have taken up RBC's (data not shown). Furthermore, the cells in these mice which have ingested RBC's, have a much lower mean fluorescence (MFI) for DiD. This implies that they have each taken up fewer RBC's. These data indicate that the macrophages which have taken up liposomal clodronate are subsequently blocked from ingesting antibody coated RBC's. This blocking effect is, of course, short-lived, because within another 18 hours these cells will all be destroyed by the clodronate. The combined effects of initially blocking, then depleting, macrophages explains the rapid onset of action for liposomal clodronate in the inventors' model.

Example 5

The following example shows that engulfed RBC's are readily seen in the macrophages of untreated mice.

In order to confirm that the flow cytometry results described above represented actual phagocytosis of RBC's and not some other process of dye acquisition, microscopy was performed on dispersed splenocytes. Dispersed cells were examined in the intact spleen, red pulp macrophages are in close contact with RBC's and it is very difficult to determine clearly whether any are intracellular.

Antibody-opsonized RBC's ($10^9$) were injected into mice which were either untreated or had received liposomal clodronate 24 hours previously. Four to eight hours later mice were sacrificed, spleens were collagenase treated, RBC's were lysed, cells were fixed and permeabilized, stained with the antibodies described below, and cytospun onto slides for microscopy. After RBC lysis, no free RBC's could be found on slides. Cells were stained with F4/80, a macrophage-specific cell surface marker, then fixed and permeabilized for intracellular staining with Ter-119 (anti-RBC). In another experiment, cells were stained intracellularly with anti-CD68 and Ter-119. Lastly, ingested CFSE-labeled RBC's were visualized due to CFSE labeling prior to injection, along with intracellular staining for CD68. As expected, the only RBC's that were seen were those that appeared to be within other cells. Few macrophages remained 24 hours after clodronate treatment. Those that were found did not appear to have ingested RBC's (data not shown). In control mice, however, macrophages were found to have ingested RBC's by three different immunofluorescent stains. These stains each revealed intact RBC's within macrophages (data not shown). CD68 was seen colocalizing with the RBC's because it is largely found in endosomes.

Example 6

The following example demonstrates that the effects of liposomal clodronate last for 1–2 weeks.

Figure 5:
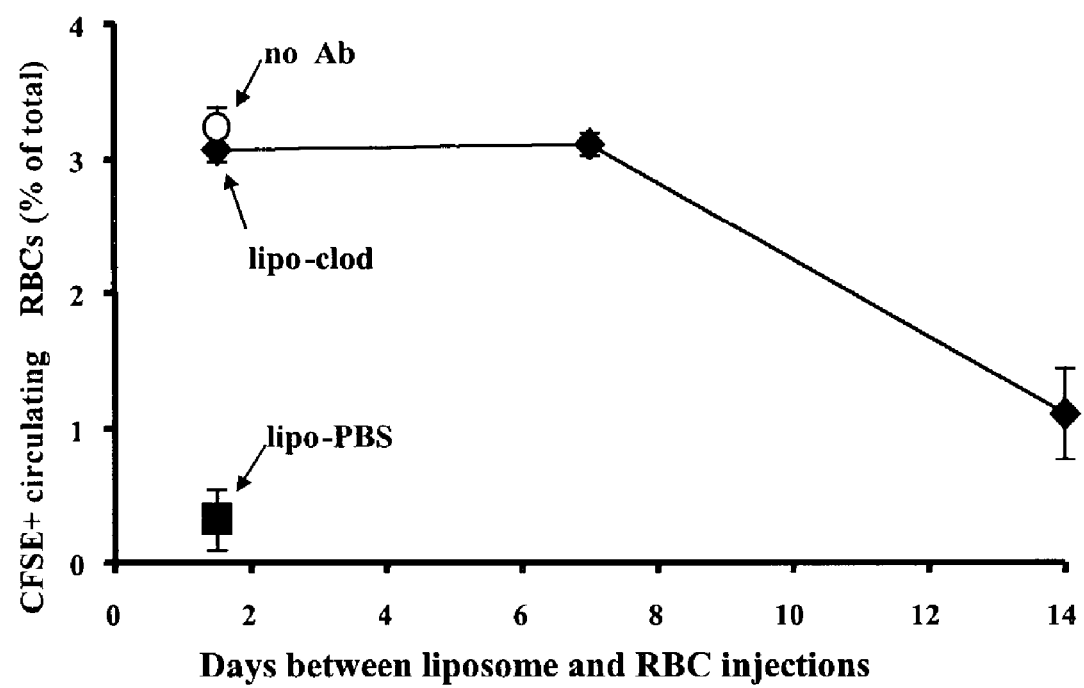
FIG. 5 is a line graph showing that a single dose of liposomal clodronate affects clearance of opsonized RBC's for 1–2 weeks.

A single dose of liposomal clodronate has previously been found to deplete splenic (red pulp) macrophages for 1–2 weeks in mice (van Rooijen et al., 1989, supra). After this period of time, natural turnover of red pulp macrophages led to the replenishment of this population. This led the inventors to wonder how long a single dose of liposomal clodronate would be effective in halting consumption of antibody opsonized RBC's. To examine this, mice were injected with clodronate liposomes and then left undisturbed for 1 or 2 weeks. They were then injected with CFSE-labeled, antibody-opsonized RBC's. Mice were bled four hours later to assess survival of circulating RBC's. Control mice received either PBS or clodronate liposomes 36 hours before RBC injection. An additional control was the injection of an identical number of non-opsonized RBC's ($5\times10^8$) into an untreated mouse. Persistence of labeled RBC's was assessed by tail bleeding 4 hours later. As can be seen in FIG. 5 (data are expressed as a percent of circulating RBC's which were CFSE positive (+/−standard error), treatment with clodronate 1 week prior to challenge with opsonized RBC's was as effective as treatment 36 hours before challenge. Treatment given 2 weeks prior to challenge was not as effective, however. These results are consistent with the persistent effects of clodronate on RBC uptake being due to macrophage depletion. As the red pulp macrophage population is replenished (in 1–2 weeks), the effects of clodronate on RBC clearance diminish.

Example 7

The following examples demonstrates that liposomal clodronate is effective over a wide range of doses.

The standard dose with which animals were treated in the experiments described in the examples above was 10 ml per kilogram of body weight (or 0.1 ml/10 grams). This dose was chosen because it has previously been shown to deplete splenic macrophages efficiently in vivo (van Rooijen et al., 1994, supra). This dose, however, may not be very practical for use in humans or large animals, because it represents a rather large infusion of liposomal drug, 700 ml for an average adult. Therefore, the inventors determined whether a smaller dose would be useful for preventing the uptake of opsonized RBC's.

Figure 6:
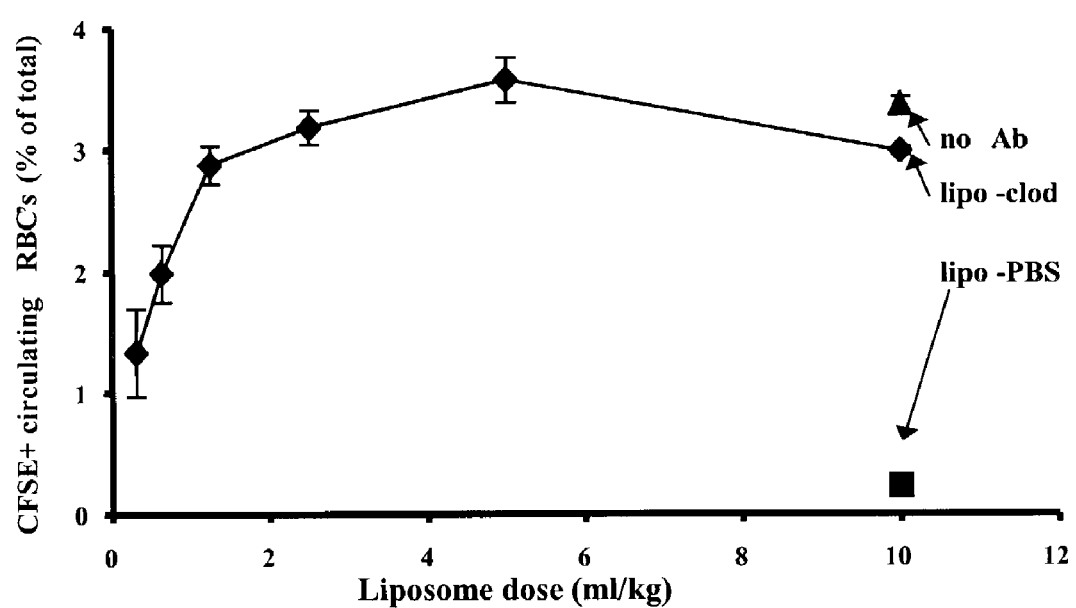
FIG. 6 is a line graph showing that liposomal clodronate is effective over a wide dose range.

In order to examine this question, mice were injected with decreasing doses of liposomal clodronate 36 hours prior to injection with opsonized, dye-labeled RBC's. Control mice received either PBS liposomes (at 10 ml/kg) or an identical number of non-opsonized RBC's (and no liposomes). Mice were bled 4 hours after injection to assess survival of circulating RBC's. FIG. 6 (data are expressed as a percent of circulating RBC's which were CFSE positive (+/−standard error)) reveals that clodronate worked equivalently from 1 to 10 ml/kg and that its efficacy dropped off below that dose. Though clodronate may not completely deplete splenic macrophages at these lower doses, it appears to be depleting (or blocking) the most actively phagocytic ones at these doses. Therefore, it maintains its efficacy over a wide range of doses and can be used at a dose that is more suitable for administration to humans and large animals.

All references and publications disclosed herein are incorporated by reference in their entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to treat antibody-induced anemia in which phagocytic cells phagocytose red blood cells, consisting essentially of administering to a patient that has antibody-induced anemia in which phagocytic cells phagocytose red blood cells a composition comprising bisphosphonate and a liposome.

2. The method of claim 1, wherein said antibody-induced anemia is autoimnume hemolytic anemia (AIHA).

3. The method of claim 1, wherein said patient has acute autoimmune hemolytic anemia.

4. The method of claim 1, wherein said bisphosphonate is selected from the group consisting of clodronate (dichloromethylene diphosphonate), alendronate, etidronate, tiludronate, pamidronate, ibandronate, zoledronic acid, and risedronate, and biologically active analogs thereof.

5. The method of claim 1, wherein said bisphosphonate is clodronate (dichloromethylene diphosphonate) or a biologically active analog thereof.

6. The method of claim 1, wherein said liposome comprises cholesterol.

7. The method of claim 1, wherein said composition is administered to said patient by a route of administration selected from the group consisting of: intraperitoneal, intravenous, subcutaneous and oral.

8. The method of claim 1, wherein said composition is administered to said patient by intravenous delivery.

9. The method of claim 1, wherein said composition is administered to said patient by intrasplenic delivery.

10. The method of claim 1, wherein said bisphosphonate is administered in an amount sufficient to reduce the numbers of splenic and hepatic phagocytic macrophages in said patient by at least about 10%.

11. The method of claim 1, wherein said composition is administered in an amount that reduces clearance of opsonized red blood cells in said patient within about 1 hour of administration of said composition, as compared to in the absence of said composition.

12. The method of claim 1, wherein said composition is administered in an amount that reduce red blood cell depletion in said patient by at least about 5%, as compared to in the absence of said composition.

13. The method of claim 1, wherein said bisphosphonate is administered in an amount of at least about 1 ml of said composition comprising about 0.7M bisphosphonate per kg body weight of said patient.

14. The method of claim 1, wherein said bisphosphonate is administered in an amount of from about 1 ml to about 10 ml of said composition comprising about 0.7 M bisphosphonate per kg body weight of said patient.

15. The method of claim 1, wherein said bisphosphonate is administered in an amount of at least about 1 mg per kg body weight of said patient.

16. The method of claim 1, wherein said composition is administered at intervals of from about 1 to 2 weeks.

17. The method of claim 1, wherein said method further comprises administration of a corticosteroid.

18. The method of claim 1, wherein said patient has had or will have a splenectoiny.

19. A method for the treatment of autoimmune hemolytic anemia (AIHA), consisting essentially of administering to patient that has AIHA a composition comprising a bisphosphonate, a liposome, and a corticosteroid.

20. The method of claim 19, wherein said bisphosphonate is selected from the group consisting of clodronate (dichloromethylene diphosphonate), alendronate, etidronate, tiludronate, pamidronate, ibandronate, zoledronic acid, and risedronate, and biologically active analogs thereof.

21. The composition of claim 19, wherein said bisphosphonate is clodronate (dichloromethylene diphosphonate) or a biologically active analog thereof.

* * * * *